(12) United States Patent
Russo

(10) Patent No.: US 8,353,895 B2
(45) Date of Patent: Jan. 15, 2013

(54) CLOSED SYSTEM IRRIGATION CONNECTOR FOR URINARY CATHETERS

(76) Inventor: Ronald D Russo, Barrington, RI (US)

( * ) Notice: Subject to any disclaimer, the term of this patent is extended or adjusted under 35 U.S.C. 154(b) by 1319 days.

(21) Appl. No.: 11/274,995

(22) Filed: Nov. 16, 2005

(65) Prior Publication Data
US 2006/0064065 A1 Mar. 23, 2006

Related U.S. Application Data

(63) Continuation-in-part of application No. 10/402,207, filed on Mar. 29, 2003, now abandoned.

(60) Provisional application No. 60/372,728, filed on Apr. 16, 2002, provisional application No. 60/391,906, filed on Jun. 27, 2002.

(51) Int. Cl.
| A61M 1/00 | (2006.01) |
| A61M 25/16 | (2006.01) |
| A61M 25/18 | (2006.01) |
| A61M 39/00 | (2006.01) |
| A61M 39/10 | (2006.01) |

(52) U.S. Cl. .......................................... 604/533; 604/34
(58) Field of Classification Search ..................... 604/30, 604/34, 99.02, 167.03, 167.04, 167.06, 236, 604/237, 240, 243, 533–539
See application file for complete search history.

(56) References Cited

U.S. PATENT DOCUMENTS

| 3,994,293 | A | * | 11/1976 | Ferro | 604/83 |
| 5,147,305 | A | * | 9/1992 | Nakamura et al. | 604/110 |
| 5,254,097 | A | * | 10/1993 | Schock et al. | 604/167.04 |
| 5,857,999 | A | * | 1/1999 | Quick et al. | 604/107 |
| 6,165,168 | A | * | 12/2000 | Russo | 604/533 |

* cited by examiner

*Primary Examiner* — Nicholas Lucchesi
*Assistant Examiner* — Nathan R Price
(74) *Attorney, Agent, or Firm* — Robert J Doherty

(57) ABSTRACT

A closed system irrigation connector for use with both 3-way and 2-way urinary catheters is disclosed. The connector fits all urinary catheters and accepts continuous irrigation sets as well as all bulb, piston, and Toomey catheter tip irrigation syringes. The connector eliminates the use of catheter plugs and reduces the mess and leakage often associated with present urinary catheter irrigation procedures. The connector converts an open procedure to a closed system procedure protecting the patient from outside contamination to reduce urinary tract infections as well as the clinician from potentially infectious body fluids. It comprises an assembly of a plastic housing with an internal silicone diaphragm slit valve and a plastic entrance port that are unitized in assembly by sonic welding. The entrance port forms a tapered wedge lock engagement with irrigation sets as well as catheter tip irrigation syringes.

9 Claims, 14 Drawing Sheets

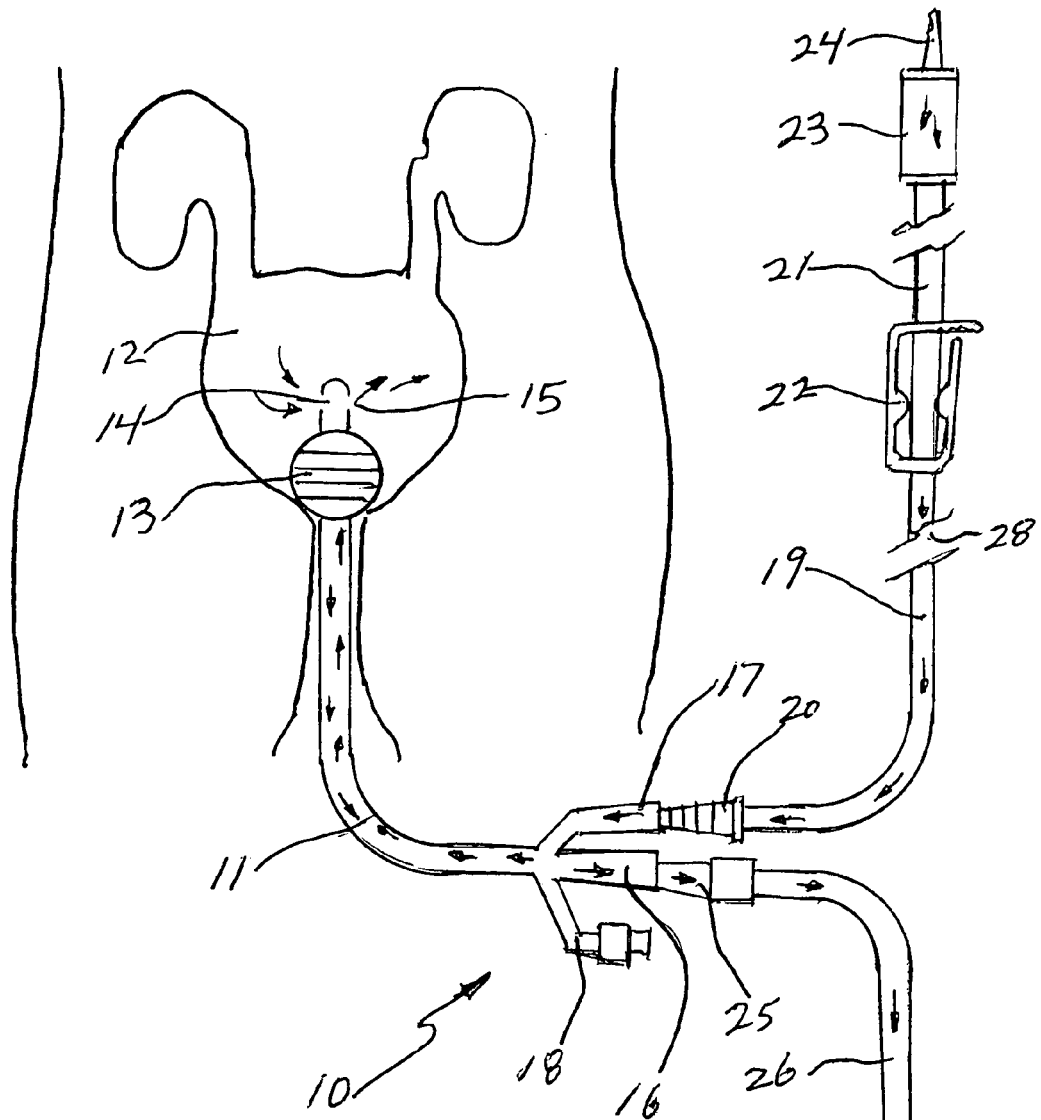
PRIOR ART Continuous Irrigation in 3-Way Urinary Catheter
FIG. 1
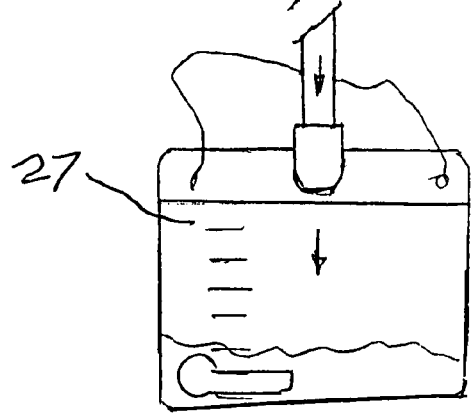

PRIOR ART Continuous Irrigation
in 3-Way Urinary Catheter

PRIOR ART Catheter Tip Syringe Irrigation
in 3-Way Urinary Catheter

PRIOR ART Catheter Tip Syringe Irrigation
in 2-Way Urinary Catheter

CLOSED SYSTEM IRRIGATION CONNECTOR FOR URINARY CATHETERS

RELATED APPLICATIONS

This application is a Continuation-In-Part of U.S. patent application Ser. No. 10/402,207 filed Mar. 29, 2003 now abandoned which in turn claims the full benefit of the following U.S. Provisional Patent Applications: U.S. Patent Application No. 60/372,728 entitled CLOSED SYSTEM URINARY CATHETER ADAPTER filed Apr. 16, 2002; and U.S. Patent Application No. 60/391,906 entitled SIDE-PORT CLOSED URINARY CATHETER ADAPTER filed Jun. 27, 2002.

BACKGROUND OF THE INVENTION

Interventional surgical procedures in the urinary tract system such as prostate surgery or trans-urethral resection typically require the insertion of an indwelling urological catheter for bladder drainage and to permit irrigation of the bladder. Urological catheters can be either 3-way and 2-way foley catheters or suprapubic catheters that are inserted through the abdomen into the bladder. Foley catheters used in these surgical procedures are called 3-way catheters in that they have three ports having a center port for drainage, a first side port for inflating the internal retention balloon, and a second side port for infusion of irrigation fluid and for aspiration of blood clots. The center port is usually attached to a drainage bag for collection of drainage. The second side port is called the irrigation access port, which is sealed closed with the insertion of a simple plastic catheter plug. Blood clots and accumulated body tissue within the bladder need to be flushed out through the irrigation port using continuous irrigation or catheter tip irrigation syringe of 60 cc capacity. Irrigation syringes are either the squeeze bulb type or the piston type, but all irrigation syringes have a large bore tapered catheter tip. These irrigation syringes with catheter tips have no standard dimensions and vary as to length and degree of taper. Postoperative recovery of the urological surgical patient can take up to several weeks and requires repeated catheter irrigations as often as once every hour. This means that the catheter plug must be removed to insert the irrigation syringe that causes the clinician to come in contact with potentially infectious urinary drainage fluid opening the urinary drainage system is often the cause of introducing outside contamination in the body that can cause urinary tract infections. As such, the current catheter plug device is messy and presents difficulties for both the patient and clinician.

The usual practice is to use a continuous irrigation set attached directly into the side irrigation port of a 3-way foley catheter to deliver a continuous stream of irrigation fluid through the catheter into the bladder. After about 24-48 hours continuous irrigation is discontinued and catheter tip intermittent irrigation is substituted.

Two-way foley catheters are more prevalent since they are more compact and clinicians believe that opening and closing the irrigation port on a 3-way catheter can promote more urinary tract infections. The one major advantage of a 3-way foley catheter, however, is that the clinician does not have to disconnect the catheter from the urinary drainage connector and bag in order to irrigate the catheter and bladder. As such, the 2-way catheter must be disconnected from the drainage bag if irrigation of the catheter or bladder is necessary to flush out blockages of the catheter or debris in the bladder. This disconnection of the catheter from the drainage bag is a well-documented cause of urinary tract infections as well as a messy procedure that exposes the clinician to potentially infectious urine. Also, disconnection and intermittent syringe irrigation of a 2-way foley catheter requires considerable nursing skill, expense, and expertise to accomplish.

To date, the inventor is not aware of any prior art inventions specifically designed to provide a closed system irrigation connector for urinary catheters. The prior art, however, is filled with inventions for intravenous syringe ports, needleless I.V. access ports for small bore luer tip or luer lock syringes, or closed adapters for delivery of enteral formula.

Reference should be made to recently issued U.S. Pat. No. 6,344,033 to Jepson et al titled "Needleless Connector" which describes in detail valves and connectors used in IV. Therapy and is very comprehensive in listing all the prior art patents and inventions.

Also, U.S. Pat. No. 6,165,168 to Russo issued Dec. 26, 2000 and its referenced patents should also be considered. With all of this it is important to note that no commercial product has been invented or is commercially available which specifically addresses or solves the prevalent occurrence of urinary tract infections caused by the open type irrigation procedures presently used.

SUMMARY OF THE INVENTION

There are many luer tip and luer lock syringe closed system I.V. therapy type devices commercially available as well as some attempts at closed system enteral adapters. This is because all luer tip, luer lock, and enteral adapters have to meet ISO or ANSI standards for dimensions, tapers, and universal interconnectability. This is not the case with irrigation continuous sets or especially with catheter tip syringes since they vary considerably as to dimensions, tapers, and connectability. They do not conform to any standard.

Because of these difficulties, it is understandable that the prior art is not helpful in guiding towards a solution and to delivering a commercially acceptable product. Toward this end, the present invention overcomes and provides a versatile device for both 3-way and 2-way foley catheters and provides a truly closed system irrigation connector. It can be provided in various embodiments to be part of a 3-way catheter or available as a separate component kit that can be plugged directly into the irrigation port of the 3-way catheter. Likewise, similar versions are also disclosed for use in 2-way catheters.

The 3-way closed system irrigation (CSI) connector comprises a three-part plastic and silicone rubber assembly, which is unitized by sonic welding or solvent cement. It is designed to fit directly into the side irrigation port of a 3-way foley catheter and once connected to the port it remains as part of the catheter and need not be disconnected. It comprises a rigid plastic lower housing, an internally fitted silicone molded valve, and an upper entrance port molded from rigid plastic.

The 3-way CSI connector will accept continuous set irrigation as well as all irrigation catheter tip syringes such as bulb, piston, or Toomey type. The specially designed entrance port forms a secure taper wedge type engagement, while the silicone valve will automatically open and close upon direct insertion of the continuous irrigation set adapter or by use of a supplied universal set adapter or by any catheter tip syringe. The CSI connector will last for many months worth of irrigation procedures without leakage, backflow, or valve failure due to the design of the entrance port that protects the resilient silicone valve from failure.

Likewise the 2-way CSI connector uses the same upper entrance port and silicone valve, but has a different lower housing which permits connection to both the catheter and urinary drainage bag.

Both the 3-way CSI connector and the 2-way CSI connector are easy to use, inexpensive to manufacture, versatile, inexpensive to the user, and provide considerable benefit to the patient and clinician.

It is therefore a primary object to provide a device that creates and maintains a closed system irrigation device in urinary catheters.

It is another object to provide a connector that is single patient use and disposable.

It is another object to provide a connector which remains a part of a urinary catheter system where there is no need to disconnect to irrigate thus reducing potential urinary tract infections and to reduce leakage and mess.

It is another object to provide a connector that will simplify the entire irrigation procedure from initial continuous irrigation on through subsequent catheter tip syringe irrigations.

It is another object to provide a connector that will protect the clinician from splash back and infectious blood tinged urine.

It is another object to provide a connector that eliminates the need for catheter plugs.

It is another object to provide a connector which will accept continuous irrigation as well as accept all catheter tip syringes whether bulb, piston, or Toomey type.

It is another object to provide a connector that will fit all types of foley catheters.

It is another object to provide a connector which will provide catheter tip irrigation into a 2-way foley catheter without disconnect which will provide a secure, leak proof, connection to both the catheter and the continuous irrigation set as well as all different types of catheter tip syringes. These and other objects will become readily apparent upon review of the drawing and detailed description of the invention.

BRIEF DESCRIPTION OF THE DRAWINGS

In the drawings which illustrate the best mode presently contemplated for carrying out the present invention:

FIG. 1 is a frontal view of the typical prior art continuous irrigation a 3-way urinary catheter system attached to a patient;

DETAILED DESCRIPTION OF THE INVENTION

Figure 2:
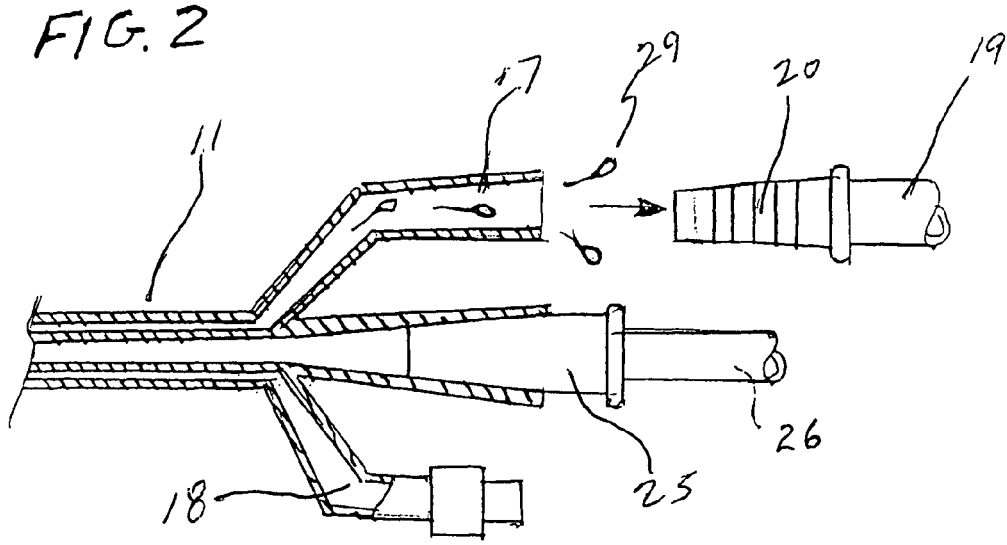
FIG. 2 is a partial cross sectional view of the typical prior art continuous irrigation in a 3-way foley catheter when the irrigation adapter is disconnected from the catheter.

FIG. 1 clearly depicts the typical prior art 3-way urinary catheter system 10 set up for continuous irrigation. This system 10 is usually set up post operatively in the operating room after completion of the invasive urological surgical procedure.

Three-way foley urinary catheter 11 is placed in the bladder 12 and is held in place by inflated balloon 13 at its distal end. Directly in front of balloon 13 is main drainage exit hole 14 and small irrigation hole 15. Both exit hole 14 and small hole 15 run the full length of 3-way catheter 11 and terminate in proximal main drainage funnel end 16 and proximal small side irrigation funnel 17. A separate inflation port 18 is used to inflate and deflate balloon 13.

Accessing irrigation funnel 17 is continuous irrigation set 19 that connects to side irrigation funnel 17 by distal connector 20. Irrigation set 19 has a large lumen flow path 28, which is maintained throughout the set 19 to deliver a large constant flow of irrigation fluid typically saline. Tubing line 21 on set 19 has a flow path of about 0.190 inches and is about 80 inches in length and is usually suspended on an I.V. pole (not shown).

Fluid flow through line 21 is controlled by adjustable pinch or roller clamp 22. Line 21 terminates in drip chamber 23 having solution container spike 24. Spike 24 pierces solution container or bag (not shown) and delivers solution into line 21 and into irrigation funnel 17 and through 3-way catheter 11.

Concurrently, irrigation fluid and resected bladder tissue drains out through main drainage funnel end 16, through distal drainage adapter 25, part of drainage line 26 which is part of urinary drainage bag 27.

FIG. 2 is a more detailed cross sectional view of prior art continuous irrigation in a 3-way foley urinary catheter 11 showing side irrigation funnel 17, inflation port 18, distal connector 20 being a part of irrigation set 19, and drainage adapter 25 flowing into drainage line 26. As can be seen, when irrigation set connector 20 is disconnected blood tinged urine 29 can splash back and leak out irrigation funnel 17.

Figure 3:
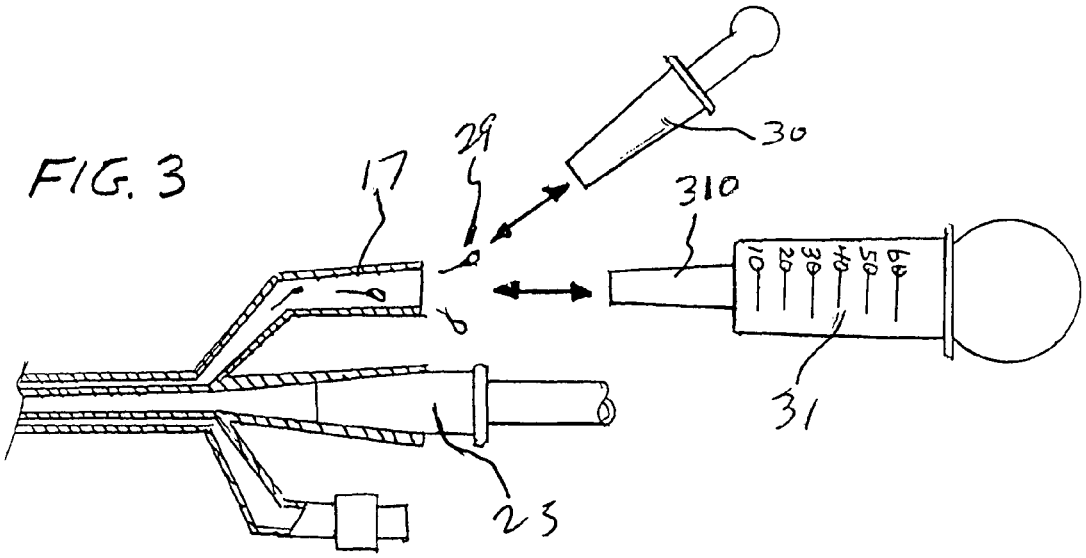
FIG. 3 is a partial cross-sectional view of the typical prior art catheter tip irrigation in a 3-way urinary catheter depicting insertion and disconnection of a catheter plug and bulb irrigation syringe.

FIG. 3 depicts prior art catheter tip syringe irrigation in a 3-way urinary catheter using a rigid plastic catheter plug 30 that is used to try to seal off irrigation funnel 17 during disconnection. Typically after the continuous irrigation procedure is completed, switching over to repeated catheter tip irrigation procedures are required several times daily for extended periods of time.

As can be seen in FIG. 3, removal and replacement of catheter plug 30 is required every time catheter tip syringe irrigation is performed. The 60 cc bulb syringe 31 has a long tapered large flow path catheter tip 31a which fits inside funnel 17.

These intermittent catheter tip syringe irrigation procedures are messy, cumbersome, and require drapes to catch spilled urine and fluid. The clinician is exposed to potentially infectious body fluids and the system must be opened up for every irrigation procedure, exposing the urinary tract to outside organisms and infection.

These existing open style irrigation procedures are perceived to be a contributing factor in the contraction of urinary tract infections in catheterized patients, leading to post operative complications, antibiotic therapy, and added hospital costs.

As such, the present invention is believed to be the first completely automatic closed system irrigation device devised which will make the entire urinary catheter system a truly closed system.

Figure 4:
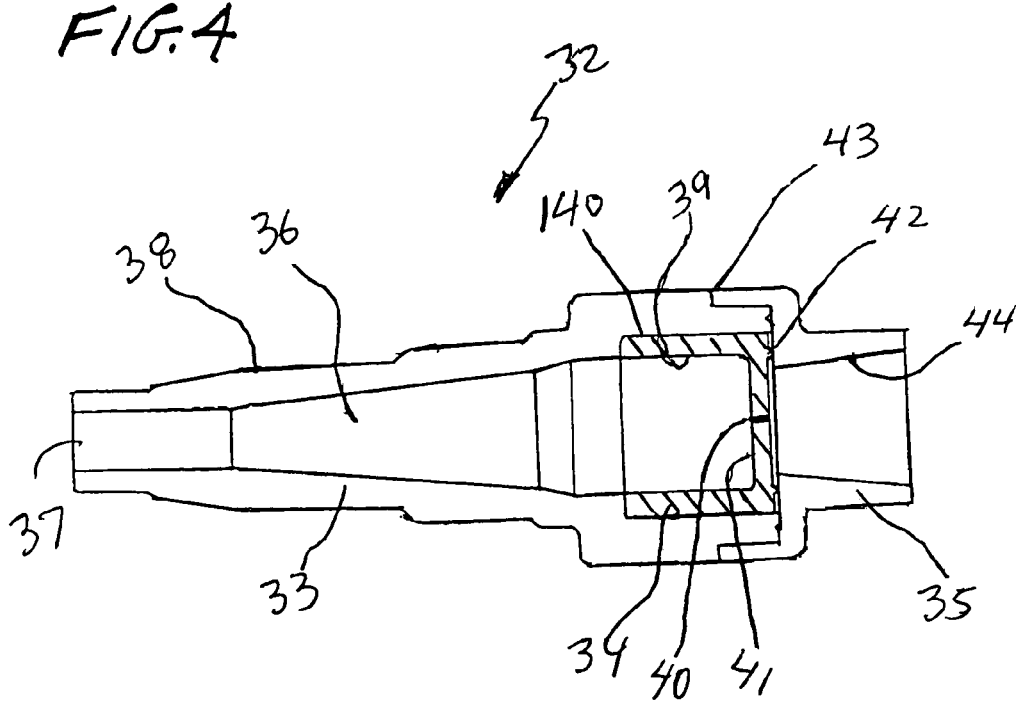
FIG. 4 is a cross sectional view of the 3-way CSI connector in its normally biased sealed closed position.

FIG. 4 is a cross sectional side view of the 3-way CSI connector 32 of the present invention comprising three components including a rigid ABS plastic injection molded lower housing 33, an internal silicone molded valve 34, and a rigid ABS plastic upper injection molded entrance port 35. Lower housing 33 has gradually tapered internal fluid flow communication path 36 exiting at lumen 37. Lumen 37 is 0.160 inches in diameter that is equal to the flow path of a catheter tip irrigation syringe. Other suitable materials may be utilized to form the connector 32.

Housing 33 has a long tapered external portion 38 which is dimensioned to give a firm oversized fit into any side irrigation port on any commercially produced 3-way foley catheter.

Silicone valve 34 is of generally cup-shaped configuration and has sidewalls 39 which are fitted into mating interior sidewalls 140 on lower housing 33. Integrally molded as part of valve 34 is diaphragm 41 about 0.050 inches thick. Through slit 40 pierces diaphragm 41 and slit 40 is about 0.325 inches in length. The valve 34 is molded from high tear strength silicone rubber, forming a resilient part.

While at first appearance valve 34 may look similar to prior art silicone-molded valves, it differs in its sealing design and technology. Molded on top of valve 34 is an upwardly extending circular seal ring 42 of a generally half round circular cross section, which is about 0.015 inches high. During assembly entrance port 35 is sonic welded to lower housing 33 at sonic joint 43. The sonic joint 43 compresses seal ring 42 downward about 0.015 inches, which forces an inward pressure on slit 40. This downward pressure on ring 42 positively biases valve 34 into a normally closed sealed position to withstand backpressure of up to 8 psi without leakage. Also, seal ring 42 acts as a top seal ring to prevent any back seepage or urine between valve side walls 39.

Upper entrance port 35 has an interior tapered entrance opening 44 at a 4½° angled opening has been found to be the ideal taper to provide a secure tapered wedge lock engagement with all types of catheter tip syringes as well as irrigation set adapters.

Figure 5:
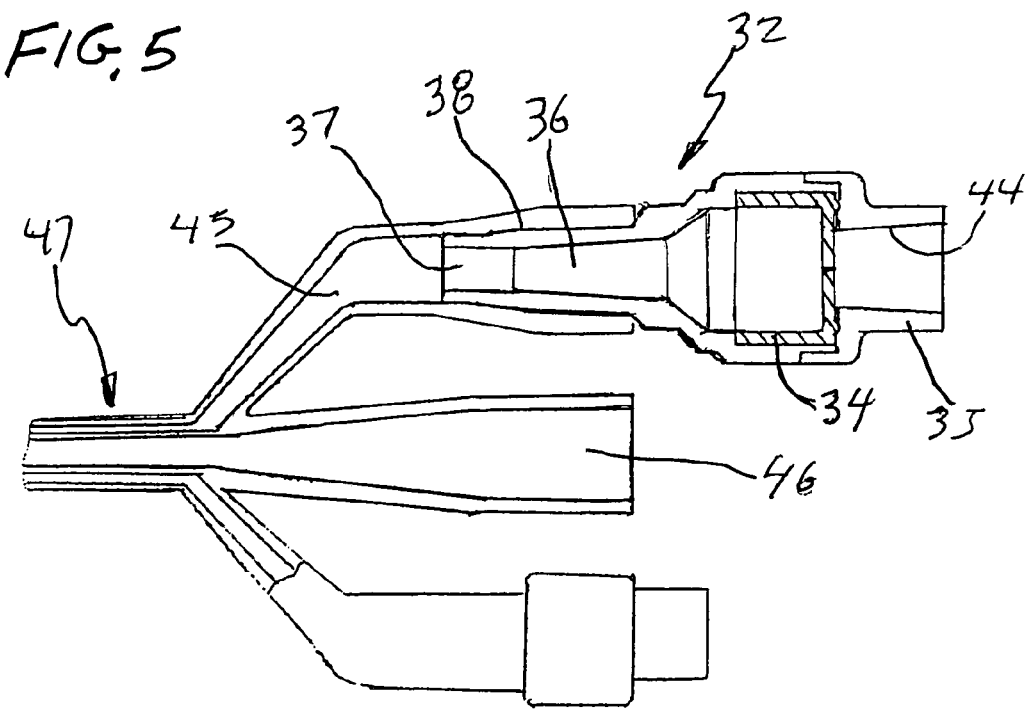
FIG. 5 is a partial cross sectional view of the 3-way CSI connector made part of the 3-way urinary catheter.

FIG. 5 shows 3-way CSI connector 32 as pre-connected part of 3-way urinary catheter 47. Connector 32 forms a normally closed sealed valve 34 sealing off entrance port 35 from fluid path 36 and internal fluid irrigation passageway 45 on catheter 47. Main funnel 46 is connectable to any urinary drainage bag.

Valve 34 keeps catheter fluid passageway 45 hermetically sealed closed to atmosphere at all times. As such, valve 34 is first positioned in a normally biased sealed closed position.

Figure 6:
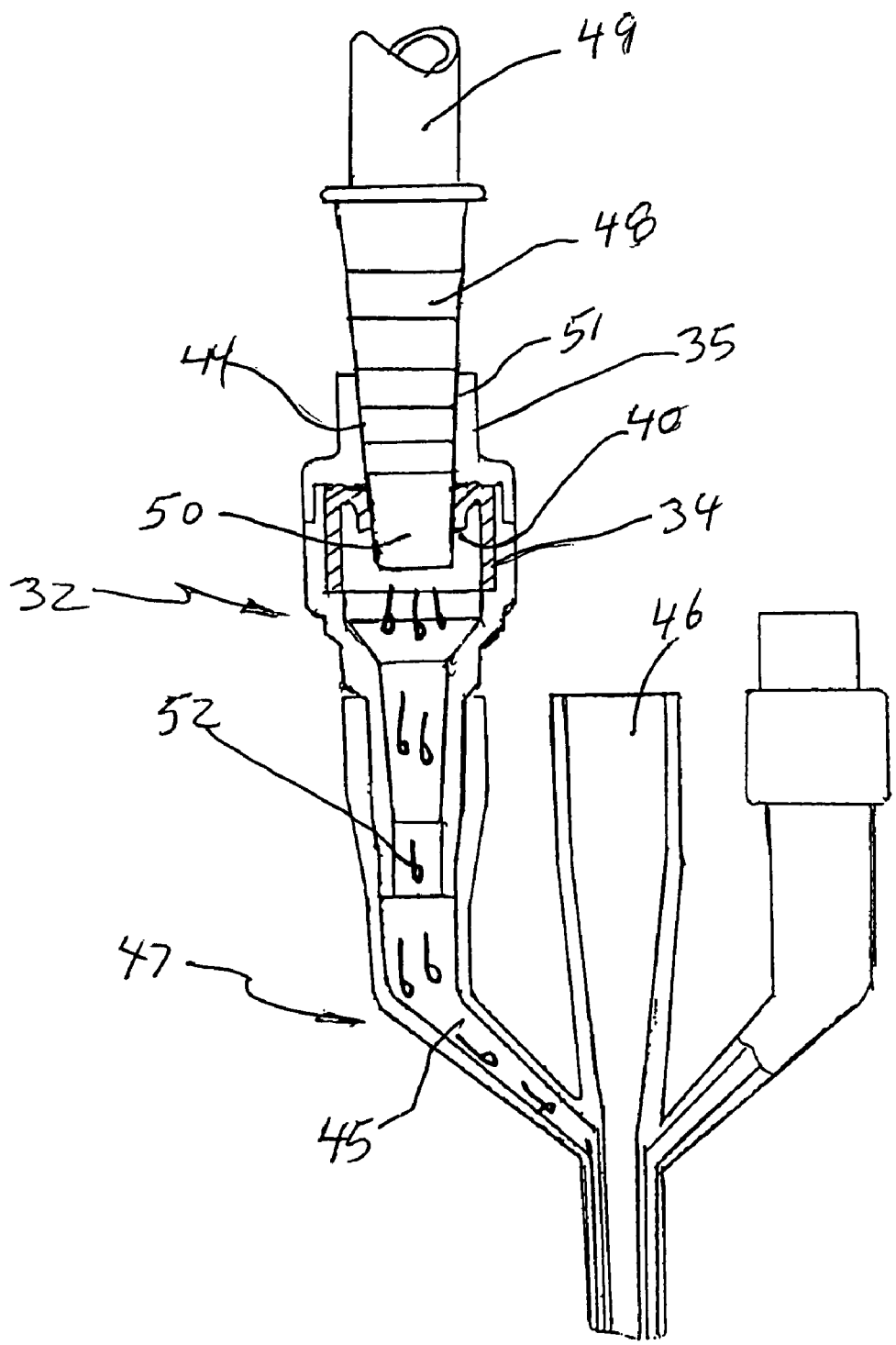
FIG. 6 is a partial cross sectional view of the 3-way CSI connector being opened by a continuous irrigation set adapter providing continuous irrigation into the catheter.

FIG. 6 depicts valve 34 being opened by continuous irrigation adapter 48 on irrigation set 49 to a second opened position wherein tip 50 on adapter 48 purses open slit 40 on valve 34. Most importantly tapered opening 44 on entrance port 35 forms a tapered wedge lock sealing engagement along the full internal engagement surface 51 within opening 44 with adapter 48 such that only the tip 50 on adapter 48 slightly purses opens slit 40. In effect, tapered adapter 48 forms a dispensing projection portion.

The tapered opening 44 at the nominal 4½° tapered opening means that the slit 40 can only be opened about ⅔ of its slit length of 0.325 inches. As such, the tapered opening 44 prevents the valve from being over stretched beyond its elastic limits that gives longevity to the valve's performance and eliminates premature failure of the valve 34. The adapter 48 is firmly press fitted and twist locked into entrance port 35 for a tight secure engagement while opening the valve 34 from its first normally sealed closed position to its second open flow path position wherein solution 52 flows into catheter fluid irrigation passageway 45. Removal of adapter 48 from entrance port 35 will enable valve 34 to automatically return to its first normally sealed closed position. While entrance port 35 is ideally molded from rigid plastic, it could also be molded from semi-rigid plastic such as PVC to be joined by solvent bonding to lower housing 33.

Figure 7:
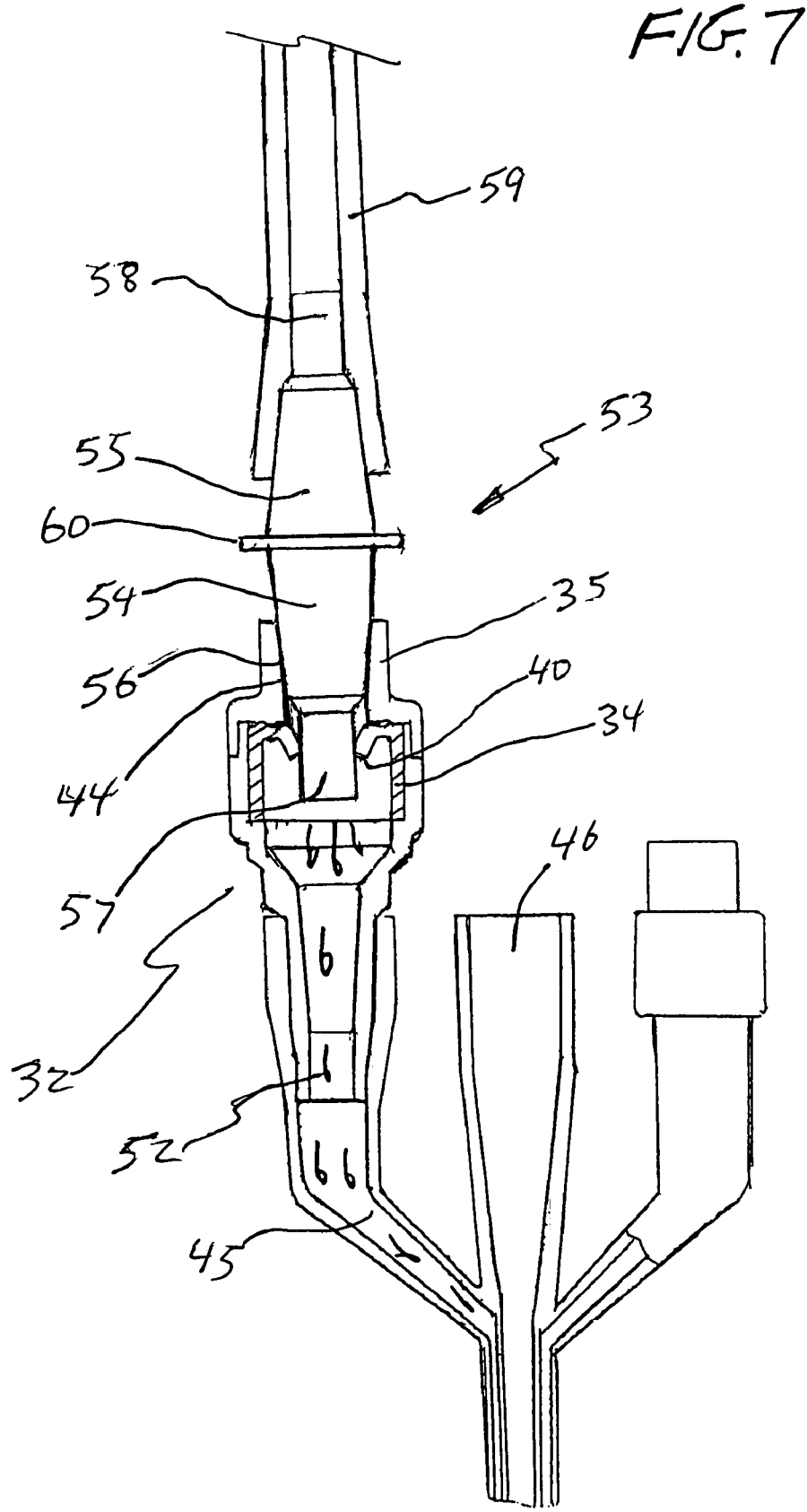
FIG. 7 is a partial cross sectional view of the 3-way CSI connector being opened by an optionally provided universal irrigation set adapter with a nominal 4° tapered tip for connection between the distal tubing on the set and connector and delivering continuous irrigation into the catheter.

FIG. 7 depicts how an optionally provided universal irrigation set adapter 53 can be used to access 3-way CSI connector 32. Adapter 53 is injection molded of ABS or polypropylene rigid plastic and has a central flange 60 and matching 4½° tapered end portions 54 and 55. Tapered portions 54 and 55 terminate in matching, that is, equal diameter, openings 57 and 58. This adapter 53 is optionally provided since some irrigation sets terminate in only silicone tubing 59 and do not have a tapered adapter depicted as 48 in FIG. 6. As such, adapter 53 is universal in that either end portions 54 and 55 will both fit tubing 59 and will form a positive secure tapered lock fit at wedge surface 56 on tapered opening 44 on entrance port 35. Either opening 57 or 58 will serve to open valve 34 and slit 40 as shown to permit irrigation solution 52 to flow into catheter passageway 45. Removal of adapter 53 will cause valve 34 to automatically return to its first normally biased sealed closed position.

Figure 8:
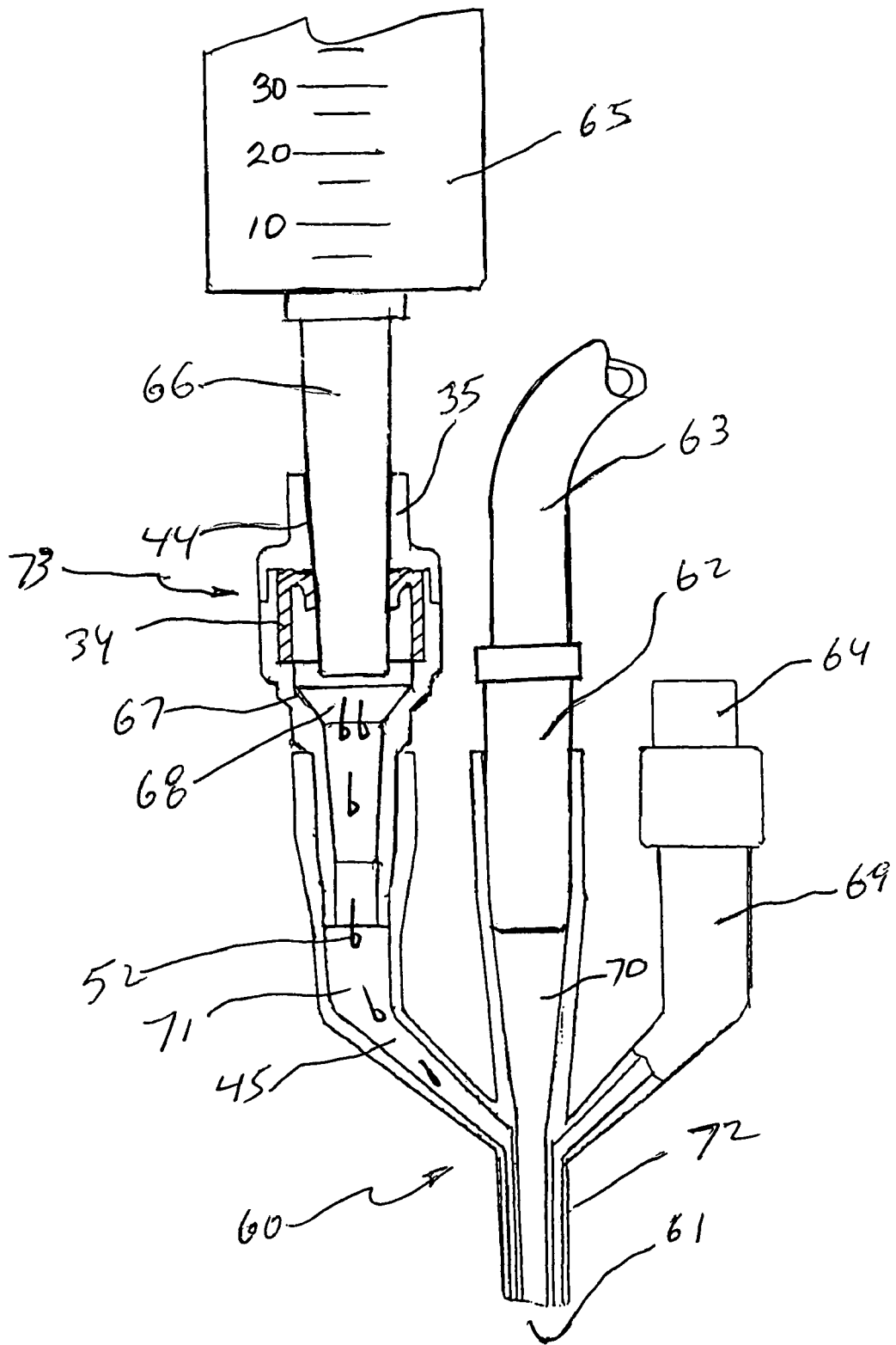
FIG. 8 is a partial cross sectional view of the 3-way CSI connector being opened by a long 4° tapered catheter tip irrigation syringe.

FIG. 8 clearly depicts a closed urinary catheter system 60 for delivering irrigation fluid 52 into a patient wherein the fluid is delivered by a large volume (60 cc to 70 cc) catheter tip syringe 65 having a long 4° tapered catheter tip 66. Tapered catheter tip 66 is press fitted and twist locked in place with matching tapered opening 44 on entrance port 35 to form a secure sealing friction fit wedge lock which is leak proof. This type of friction fit wedge lock with the catheter tip 66 is very important since catheter tip syringes such as 65 exert a high forward flow creating considerable back pressure which could easily disengage the catheter tip 66 initiating leakage and backsplash against the clinician. Unlike small bore tip luer tip or luer lock syringes, catheter tip syringes have a much larger tip opening 67 (about 0.160 inches compared to only 0.090 inches in a luer tip) which is necessary to break up bladder retained clots, tissue, and debris which must be drained out drainage tubing 63 through drainage adapter 62.

As can be seen, the distal end 61 of indwelling urological catheter 72 resides within the bladder as seen in FIG. 1, while all proximal port ends 69, 70, 71 reside outside the body and are closed off by catheter balloon inflation valve 64, adapter 62, and closed system irrigation connector 73 respectively creating a totally closed irrigation system. Note also how the catheter tip opening 67 fully opens silicone valve 34 yet its tip opening 67 is limited in its travel within connector 73. Connector 73 has lower fluid communication path 68 in fluid communication with the catheter fluid passageway 45. Valve 34 is positioned between lower path 68 and upper entrance port 35. Valve 34 is first positioned to a normally biased sealed closed position preventing fluid 52 from exiting out valve 34. However, the direct manual engagement of tip 66 causes fluid 52 to flow into passageway 45. Retraction or removal of catheter tip 66 from valve 34 within CSI connector 73 will cause valve 34 to automatically return to its first normally biased sealed closed position. In addition, syringe 65 can be used to aspirate clots or fluid sampling for laboratory analysis through passageway 45 without disconnect. In this example, tip 66 forms a dispensing projection portion.

Figure 9:
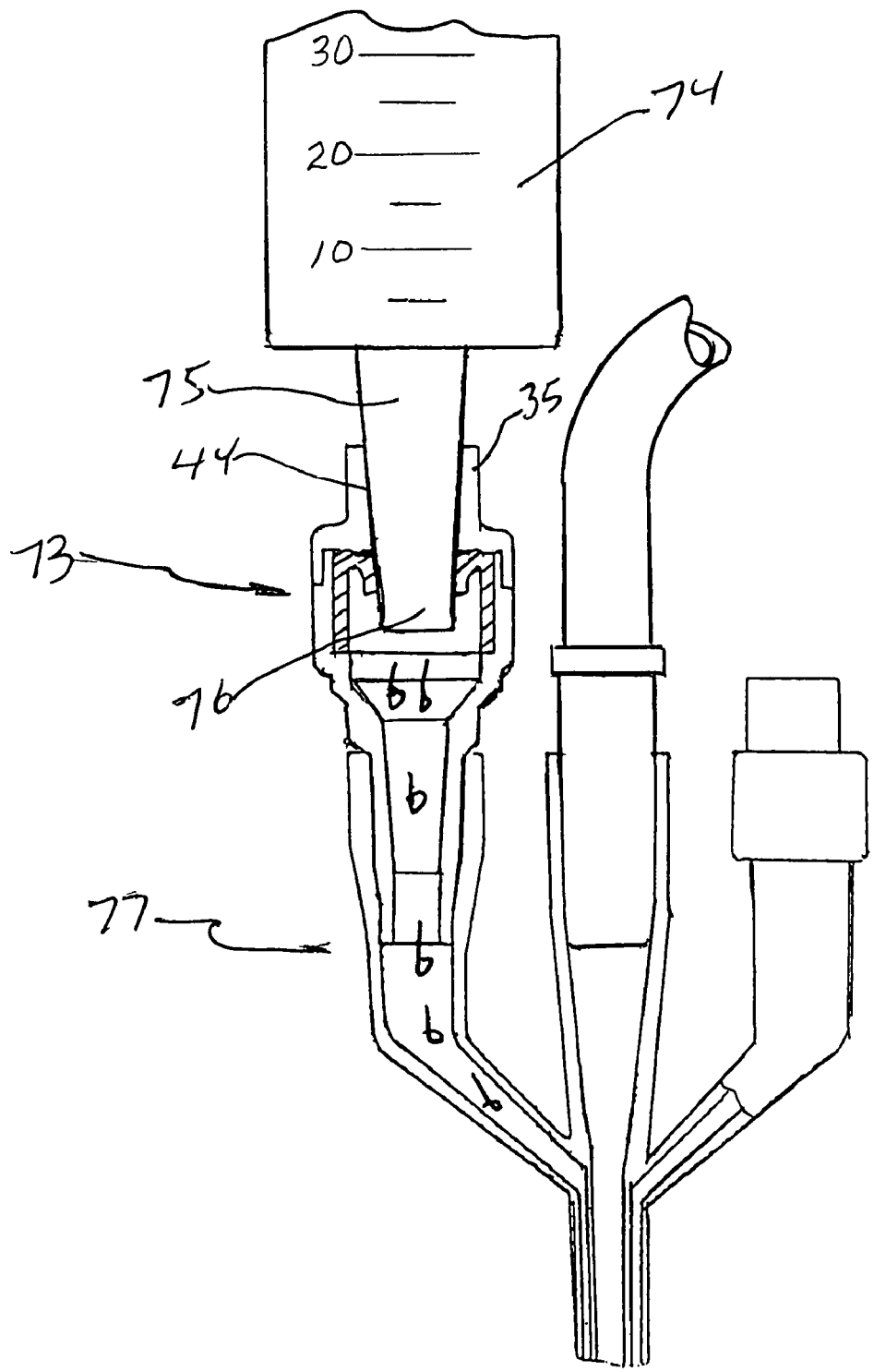
FIG. 9 is a partial cross sectional view of the 3-way CSI connector being opened by a short 4 ¾° tapered catheter tip irrigation opening.

FIG. 9 depicts the same exact system 60 depicted in FIG. 8 with the exception that a different tapered catheter tip irrigation syringe 74 is shown inserted into 3-way CSI connector 73. Syringe 74 has a 4¾° angled catheter tip 75, which still forms a wedge lock with tapered opening 44 on entrance port 35. As such, the nominal 4½ tapered angle opening 44 on entrance port 35 is capable of positive secure sealing engagement with all the non-standard, non-uniform tapered angles on various manufacturer's catheter tip irrigation syringes which vary from a tapered angle of 4° up to a tapered angle of 4¾.

The 3-way CSI connector 73 will accept all the different and varying tapered angled irrigation syringes from Bard Medical, Kendall Healthcare, Becton-Dickinson Medical, Davol Medical, Baxter Healthcare, and Medline Medical whether the syringes are bulb type, piston type, or Toomey type.

In summary, the 3-way CSI connector 73 depicted in FIGS. 8 and 9 will fit into all the various types of 3-way foley catheters and will also accept all different types of catheter tip irrigation syringes to deliver consistent, reliable performance in a system for delivering closed system irrigation into a urinary catheter and patient bladder.

Figure 10:
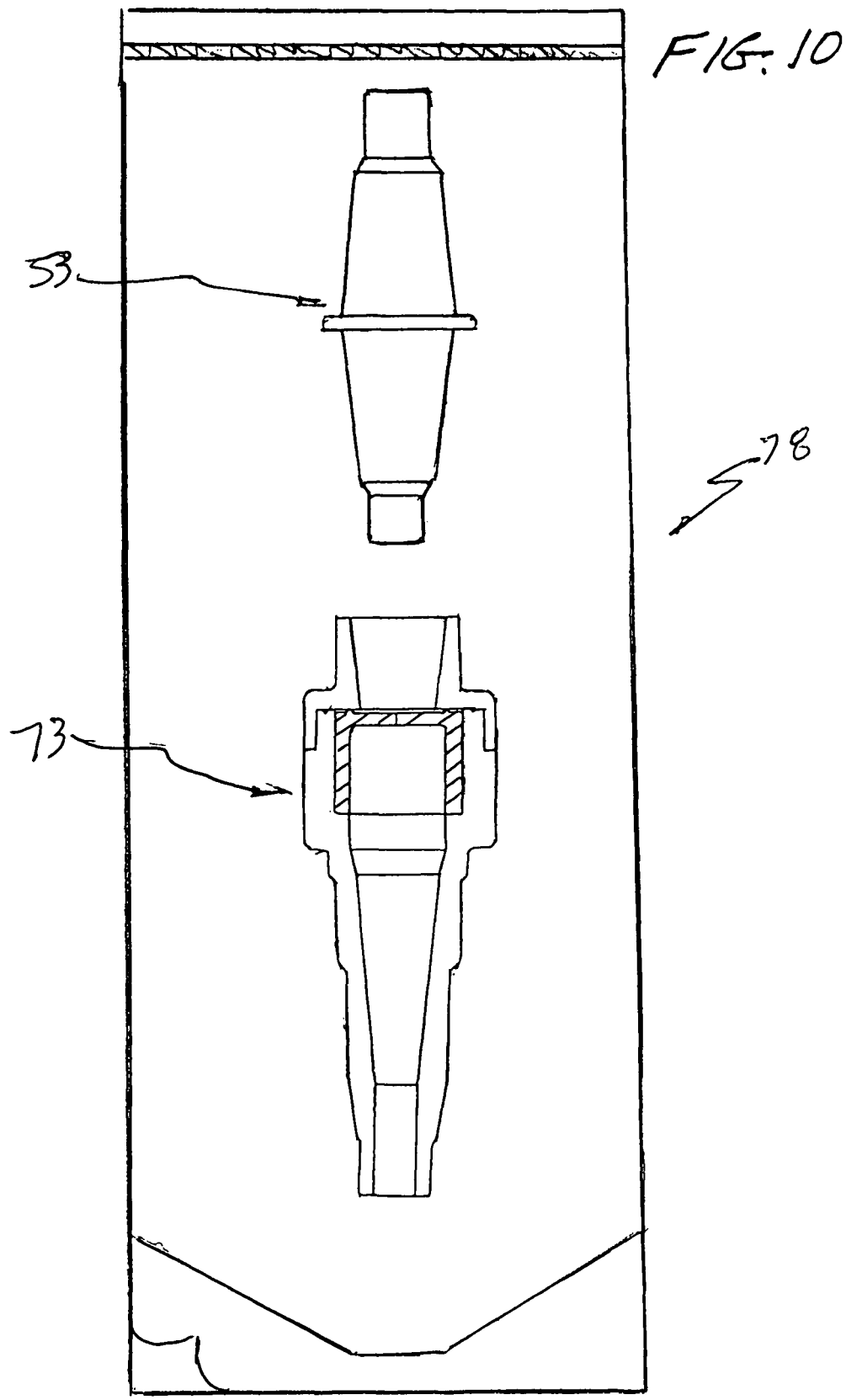
FIG. 10 is a frontal view of the 3-way CSI connector along with its optional universal irrigation set adapter packaged in a sterile packed kit.

FIG. 10 depicts sterile peel apart packaged 3-way CSI connector kit 78 having both the 3-way CSI connector 73 and universal irrigation set adapter 53 as part of its contents. Kit 78 in essence becomes a conversion kit wherein any existing manufactured 3-way urinary foley catheter can be converted into a closed system irrigation system by using the kit 78 having separate connector 73.

While a peel apart sterile package is shown, other types of sterile packaging commonly known in the medical device field such as a form, fill, and seal package or a lid stock formed tray could also be used.

Figure 11:
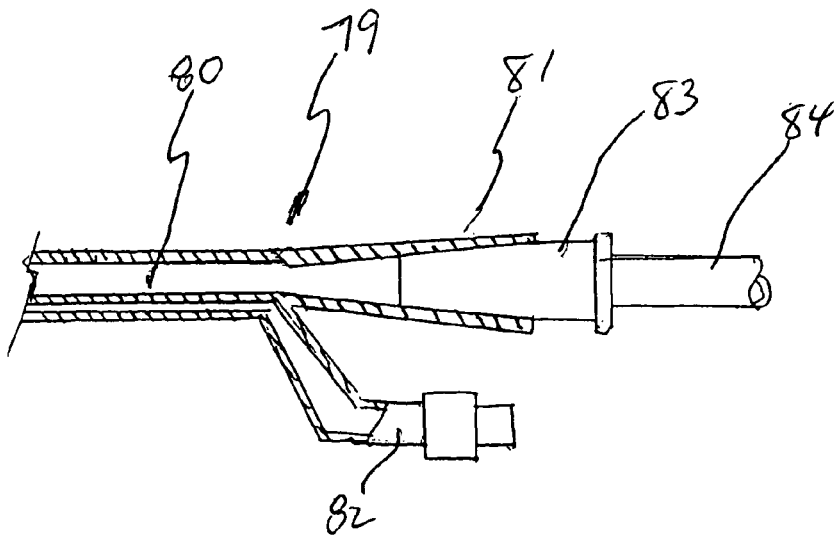
FIG. 11 is a partial cross sectional view of a 2-way urinary foley catheter attached to the distal adapter on a urinary drainage bag.

Now turning to the CSI connector's use on a 2-way urinary foley catheter there is shown in FIG. 11 a typical 2-way catheter 79 having only one large fluid passageway 80 terminating at proximal port 81 and inflation port 82. It is termed a 2-way since it terminates in only two ports compared with a 3-way that terminates in three ports. Proximal end port 81 connects directly to a urinary drainage bag adapter 83 with tubing line 84 that drains down into its urinary drainage bag (not shown).

Figure 12:
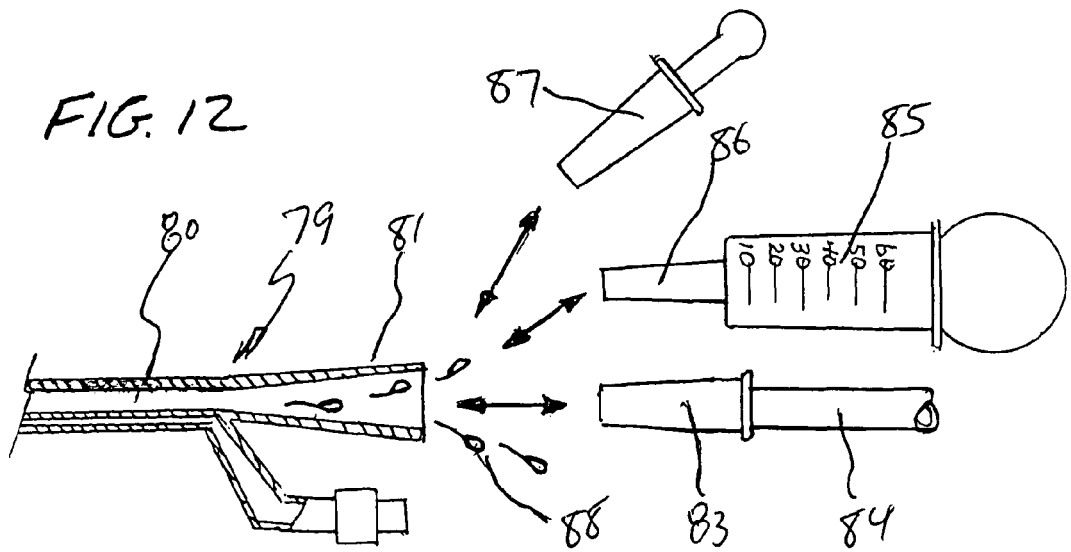
FIG. 12 is a partial cross sectional view of the typical prior art catheter tip syringe irrigation in a 2-way urinary catheter depicting insertion and disconnection of a catheter plug and bulb irrigation syringe along with the distal adapter on a urinary drainage bag having to be disconnected.

FIG. 12 depicts prior art catheter tip syringe irrigation in 2-way catheter 79. As can be seen adapter 83 must be disconnected from proximal end port 81 on catheter 79 every time irrigation is required. Irrigation bulb syringe 85 with catheter tip 86 must be inserted into port 81 for irrigation and removed upon completion of the irrigation procedure. During this connect and disconnect which must be repeated often, blood tinged urine 88 win backsplash and leak out port 81 shown.

Catheter plug 87 is usually used to seal off port 81 when the irrigation procedure is completed. As shown, the mess, contamination, and leakage associated with a 2-way foley catheter is even worse than a 3-way procedure because a high back flow of bladder drainage often spills out port 81 once catheter plug 87 is removed.

Figure 13:
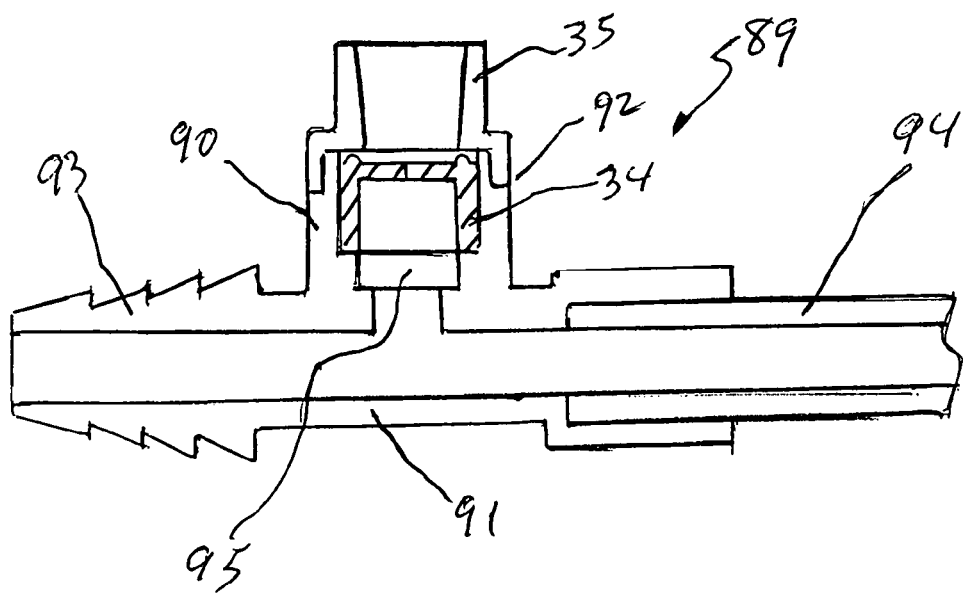
FIG. 13 is a cross sectional view of the 2-way CSI connector in its normally biased sealed closed position wherein the 2-way CSI connector becomes the distal adapter on a urinary drainage bag.

FIG. 13 shows 2-way CSI connector 89 having the same silicone molded valve 34 and entrance port 35 structure as shown in 3-way CSI connector 32 shown in FIG. 4. The only difference is that connector 89 now has a t-type of lower housing 91 having a side port 90 which houses valve 34 and entrance port 35. Port 35 is sonic welded to side port 90 at sonic joint 92. Connector 89 has rigid injection molded ABS lower housing 91 having a frontal barbed adapter portion 93 and a rearward drainage tubing 94 solvent cemented into housing 91. Lower fluid communication path 95 is in mutual fluid communication with side port 90, adapter portion 93, and tubing 94.

Figure 14:
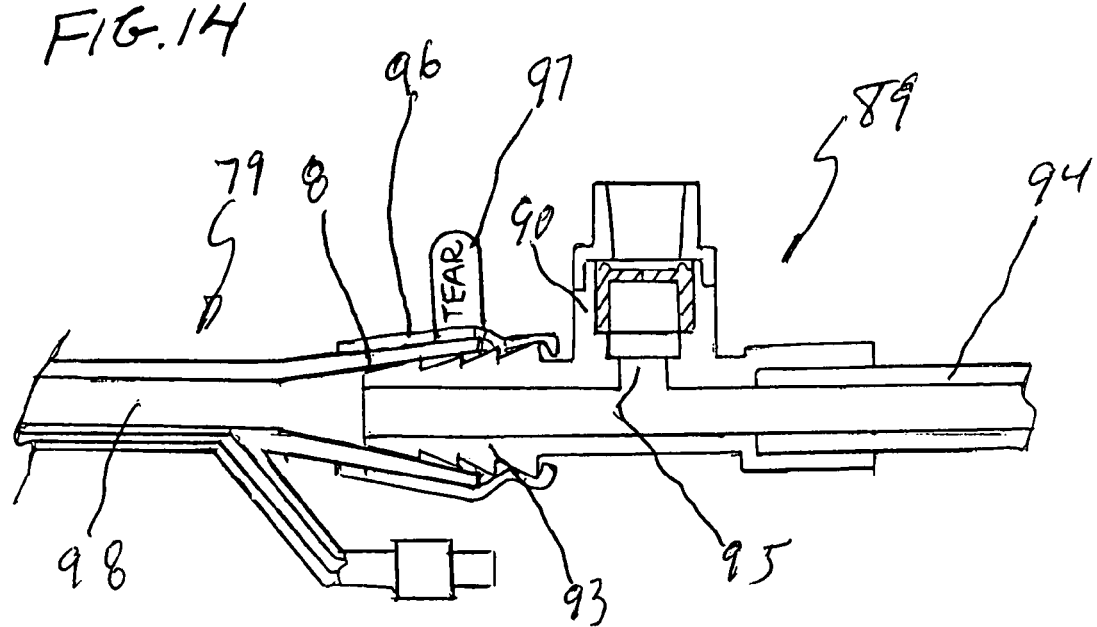
FIG. 14 is a partial cross sectional view of the 2-way CSI connector attached to a 2-way foley urinary catheter and the connector having an optional tamper proof tear indicator.

FIG. 14 depicts 2-way CSI connector 89 attached to 2-way urinary foley catheter 79 wherein connector 89 provides a closed system means for direct fluid communication between side port 90, lower path 95, and catheter fluid passageway 98 accessing a patient's bladder for either drainage or for delivering closed system irrigation into 2-way catheter 79. Also shown is tamper evident shrink band 96 which can be an optional feature indicating to various departments in the hospital that the system has not been opened. Tear tab 97 can be used to unseal the band 96 if desired.

Figure 15:
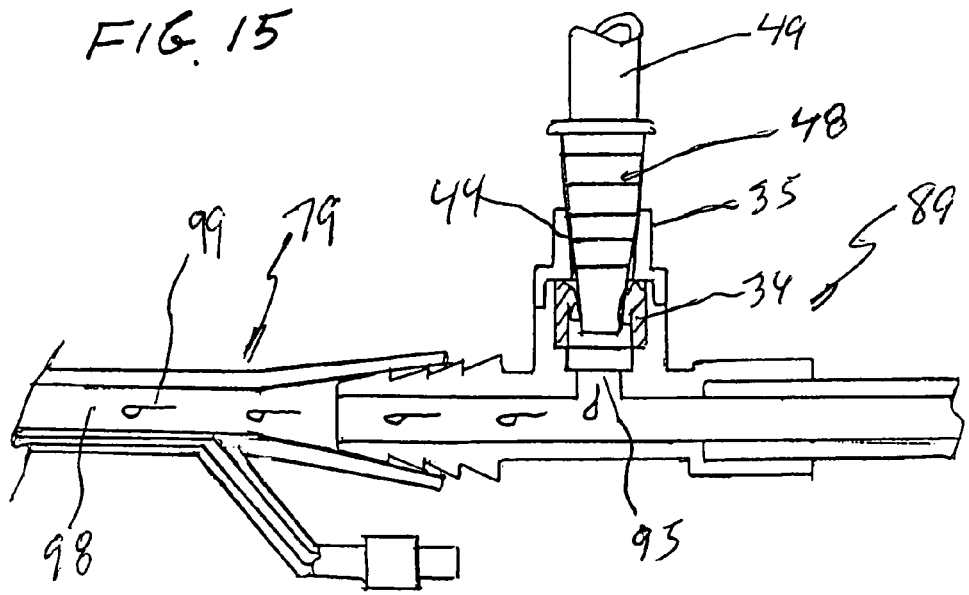
FIG. 15 is partial cross sectional of the 2-way CSI connector being opened by a continuous irrigation set adapter providing continuous irrigation into the catheter.
Figure 16:
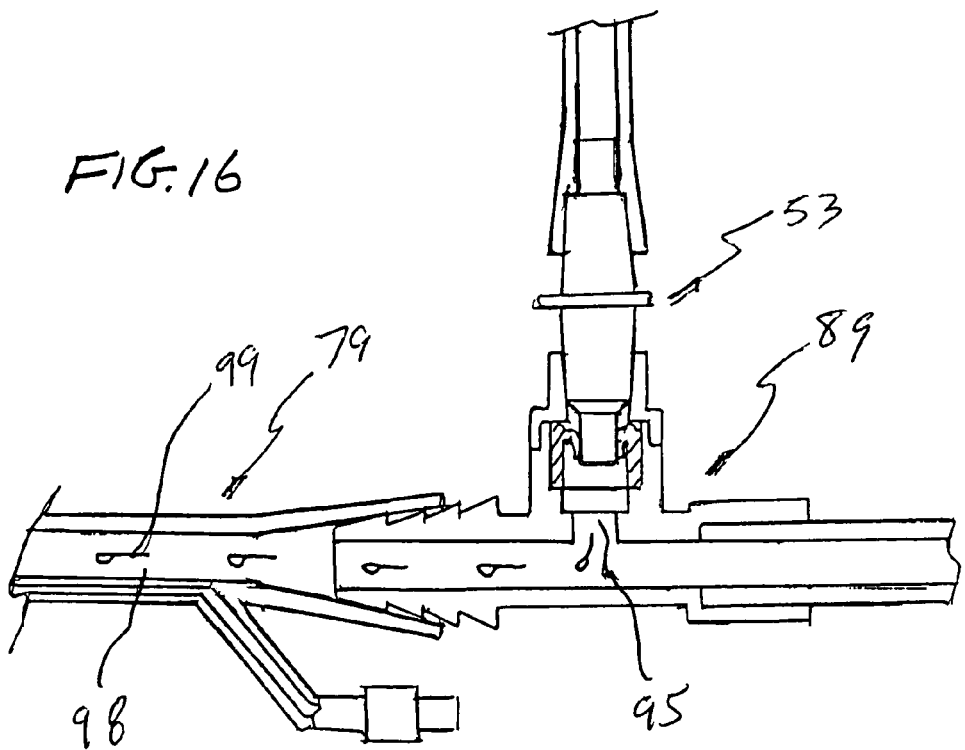
FIG. 16 is a partial cross sectional view of the 2-way CSI connector being opened by the optionally provided universal irrigation set adapter with a nominal 4° tapered tip for connection between the distal tubing on the set and the connector and delivering continuous irrigation into the catheter.

FIGS. 15 and 16 are similar in application to FIGS. 6 and 7 wherein 2-way CSI connector 89 is shown delivering irrigation fluid 99 into 2-way foley catheter either through irrigation set adapter 48 or by universal irrigation adapter 53 each of which define a dispensing projection portion.

Figure 17:
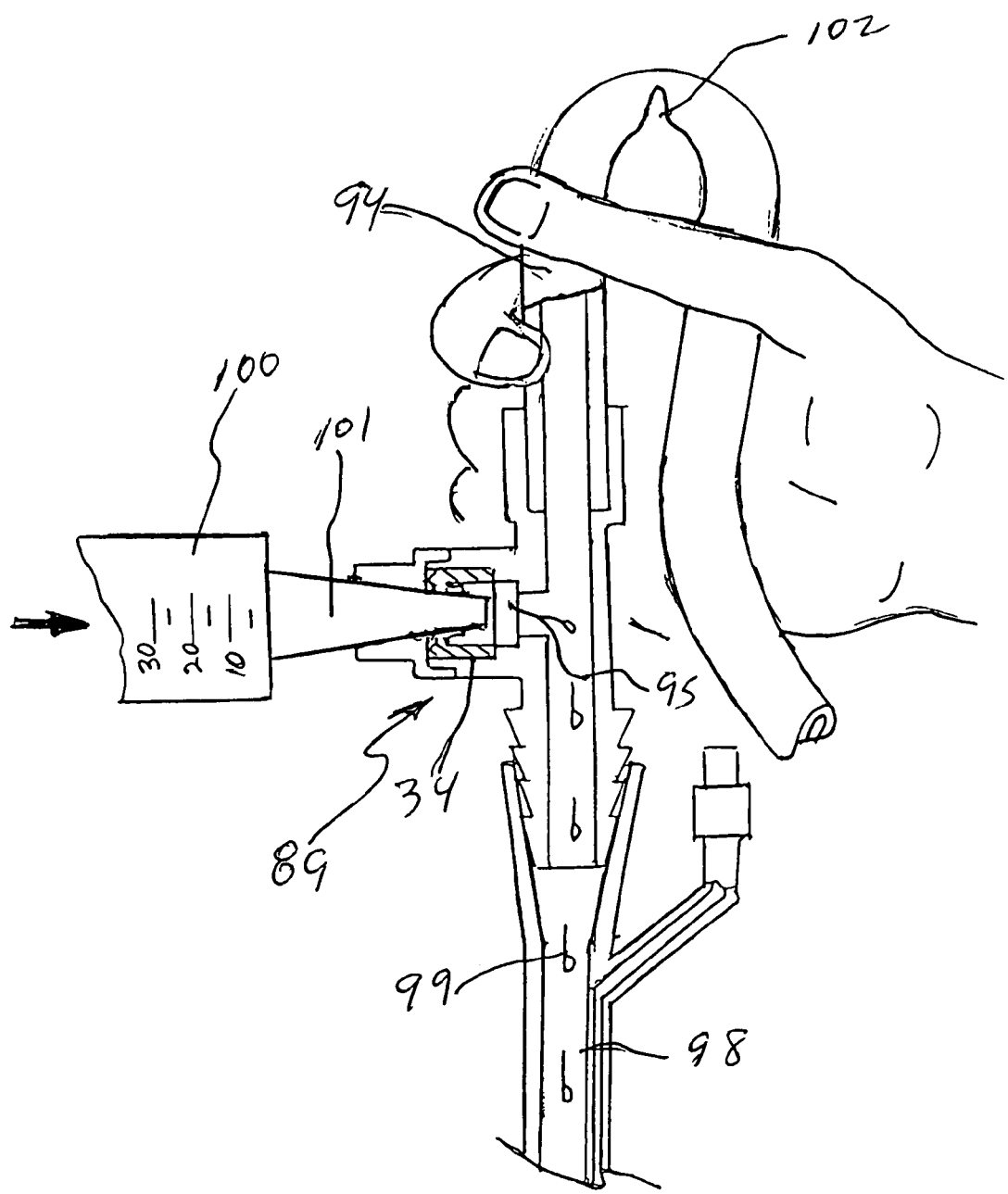
FIG. 17 is a partial side view of the 2-way CSI connector depicting a high flow power flush catheter tip syringe irrigation procedure requiring the manual kink shut off of the drainage tubing line.

FIG. 17 shows a simple tubing pinch-off technique manually applied which can direct a power surge of syringe irrigation through syringe 100 having catheter tip syringe tip 101 through connector 89 to the catheter. Just like in the 2-way version, silicone valve 34 is normally first biased to a sealed closed position and is opened by introduction of catheter tip 101 to deliver fluid 99 into lower fluid path 95 and on into catheter passageway 98. Removal of catheter tip 101 from valve 34 will automatically return valve 34 to its first closed position. Manually temporarily kinking off drainage tubing 94 at point 102 will insure that all the irrigation fluid 99 will be directed into catheter passageway 98. Also, kinking off the tubing 94 can serve to use the catheter tip syringe 100 as a means for aspiration of fluid out of the bladder and also as a means for securing a closed system urine sample from the bladder for laboratory analysis. Once the tubing is manually released then drainage can resume through tubing line 94.

Figure 18:
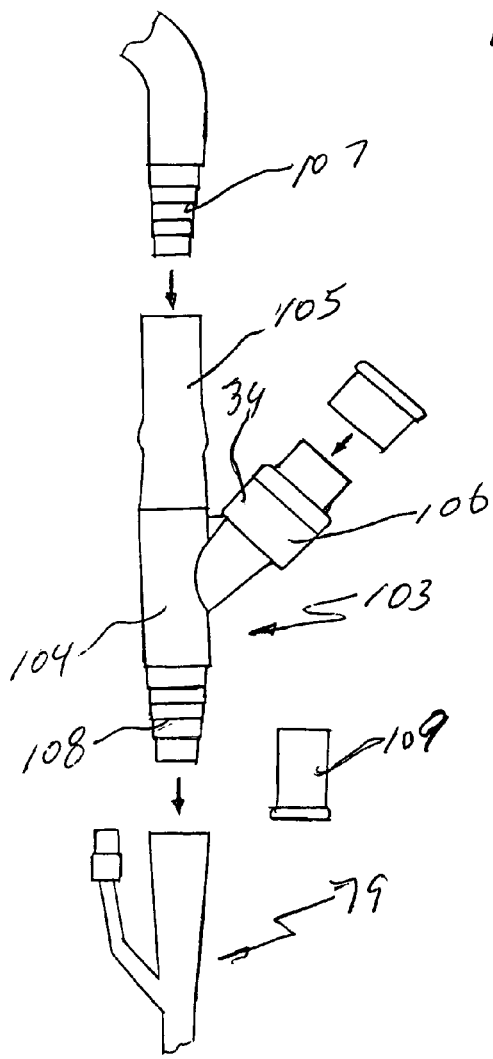
FIG. 18 is a side view of an alternate embodiment of the 2-way CSI connector wherein the connector has an angled entrance port and is a separate component connectable to any urinary drainage bag.
Figure 19:
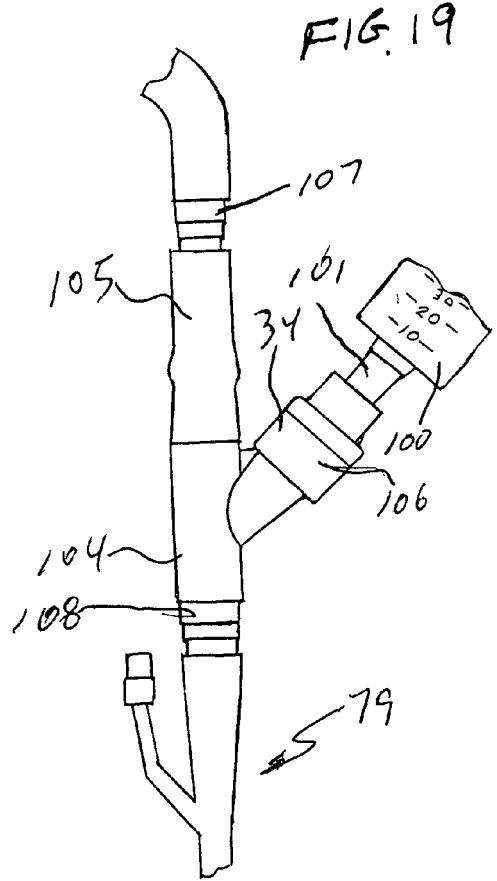
FIG. 19 is a side view of the alternate embodiment depicted in FIG. 18 wherein the 2-way CSI connector is shown connected to both the 2-way foley catheter and the urinary drainage bag adapter and also showing a catheter tip syringe inserted into the angled entrance port.

FIGS. 18 and 19 depict an alternate embodiment 103 of a 2-way CSI connector 104. This embodiment has a 45° angled side port 106 and a frontal adapter 108 connectable to 2-way catheter 79. Connector 104 is in essence a conversion connector wherein connector 104 has a rearward silicone bushing 105 that permits connection to any urinary drainage bag adapter 107. Connector 104 is a separate part.

FIG. 19 shows syringe 100 with catheter tip accessing side-port 106, which has internal silicone valve 34 (not shown). Some clinicians may prefer the 45° angled side port 106 since irrigation flow is angled towards the catheter and away from drainage adapter 107. Also, flexible closure cap 109 can be provided to cap off adapter 107 during set up of alternate embodiment 103. The alternate embodiment 103 will perform all the functions of 2-way CSI connector 89 depicted in FIGS. 15, 16, and 17.

Figure 20:
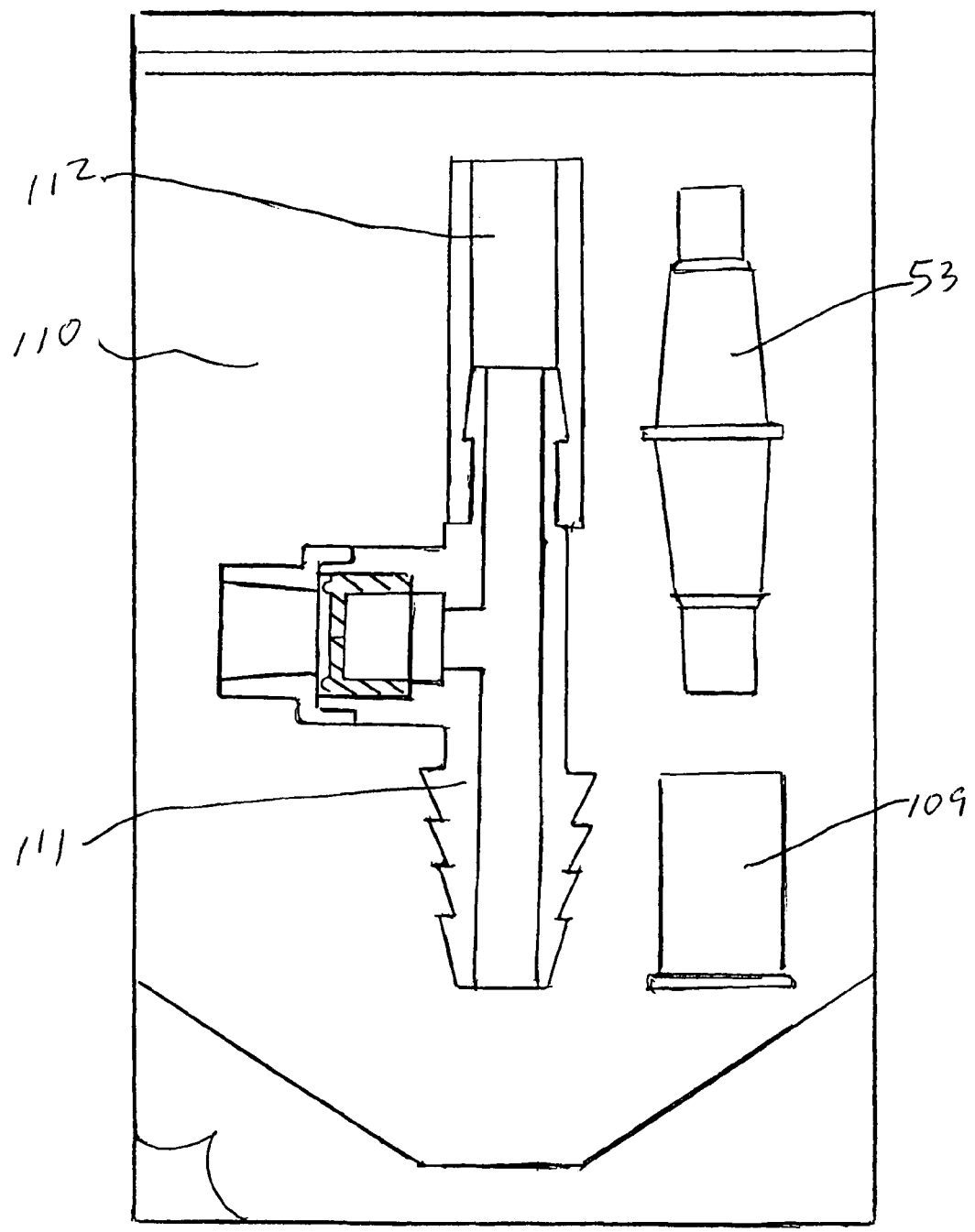
FIG. 20 is a frontal view of the 2-way CSI connector along with its optional universal irrigation set adapter and a closure cap packaged in a sterile packed kit.

FIG. 20 depicts sterile peel apart packaged 2-way CSI connector kit 110 similar in concept to kit packaged 3-way CSI connector kit 78 shown in FIG. 10. Two-way CSI connector 104 including rear bushing 112, universal adapter 53, and closure cap 109 are also part of the kit 110. Two-way CSI connector 89 may be substituted for connector 104. In essence, kit 110 becomes a conversion kit wherein any existing manufactured 2-way urinary foley catheter can be converted into a closed system catheter irrigation system by using the kit 110. Just like FIG. 10, a peel apart package is shown, but many other types of sterile packaging can be used. This 2-way CSI connector kit 110 or the pre-connected 2-way CSI connector set up depicted in FIG. 14 would be especially useful to long term foley catheter users because irrigation of the catheter is now a closed system to reduce urinary tract infections and irrigation is now a much simpler, less messy procedure which can be easily administered by the patient or by a nursing home or by home caregiver.

From the foregoing description, it is believed clear that a new, useful and non-obvious system has been devised. Referring again to U.S. Pat. No. 6,165,168, the present invention initially differs from applicant's previous patent in that the Russo '168 patent has an entrance opening formed by an O-ring that has straight sidewalls, and it is those straight sidewalls that engage the syringe (the internal tapered portion does not engage the syringe and is present only to accommodate a side core to enable the resilient valve member 14 to be conveniently removed from the mold during the injection molding thereof). Thus the Russo '168 entrance walls are straight, not downwardly inwardly tapered, as clearly shown in the various drawings of the present application. A second difference is that this tapered wall arrangement of the present invention enables the similarly tapered syringe distal tip to engage in a taper or wedge lock fit to resist fluid back pressure by resisting the upper movement of the syringe vis-à-vis the upper entrance port. The same wedge fit or taper lock additionally prevents the large diameter upper portions of the syringe from moving further into the valve and overstretching the slit-lip opening thereof.

Thus the contact of the tapered outer walls of the syringe tip 66 with the tapered inner walls of the entrance port opening 44 fixedly limits the depth of travel of the syringe tip into the slit opening in the valve and thereby prevents premature failure of the valve due to overstretching of the diaphragm 41 segments formed by the slit 40 piercing through said diaphragm and/or of the peripheral portions of the slit itself. The taper of the inner walls of the entrance port is downwardly inwardly directed at a taper angle of approximately 4½° and thus matches the similar downwardly inwardly taper of the syringe tip outer walls. It is thus believed clear that there is no teaching of this wedge lock limited travel feature of the present invention in the Russo '168 patent.

It should also be noted that variations can be made to the diaphragm slit valve in that it could be shorter in height and shaped in a rectangle or square instead of in a circular form as shown. Many variations in shape or form can also take place for other components as well as material changes without departing from the broad scope of the underlying invention. shape or form can also take place for other components as well as material changes without departing from the broad scope of the underlying invention.

I claim:

1. A closed system medical connector for use and engagement with a non-luer tip catheter tip syringe, said non-luer tip catheter tip syringe having a tapered distal tip having a total length exceeding 0.300 inches, said closed system medical connector comprising:
   an upper entrance port, the upper entrance port having both a vertical length greater than 0.300 inches and an entrance opening,
   a lower fluid communication path, and
   a valve positioned between the lower fluid communication path and the upper entrance port,
   said upper entrance port configured and dimensioned as to both said vertical length greater than 0.300 inches and said entrance opening so that said upper entrance port accepts and engages the tapered distal tip of said non-luer tip catheter tip syringe so that said tapered distal tip opens said valve to permit syringe tip fluid flow or fluid aspiration sampling from or back into the non-luer tip catheter tip syringe from said lower fluid communication path, and so that said upper entrance port prevents accepting of or engagement with smaller bore and shorter length uniform standardized dimensioned tapered tips of luer tip or luer lock syringes as defined by ISO/ANSI 1986 standards by preventing said smaller bore and shorter length uniform standardized dimensioned tapered tips of said luer tip or luer lock syringes from reaching beyond said vertical length greater than 0.300 inches of said upper entrance port and thereby preventing contact with said valve to prevent said closed system medical connector from being used as an I.V. administration device by said luer tip or luer lock syringes.

2. The closed system medical connector of claim 1, wherein the vertical length greater than 0.300 inches extends between said entrance opening of said upper entrance port and said valve and is greater than the length of the tapered tip of any of said luer tip or luer lock syringes.

3. The closed system medical connector of claim 1, wherein said upper entrance port forms a sealing engagement with said tapered distal tip of said non-luer tip catheter tip syringe to open said valve and to prevent disengagement of said tapered distal tip with said upper entrance port caused by back pressure during use of said non-luer tip catheter tip syringe.

4. The closed system medical connector of claim 1, wherein said upper entrance port forms a sealing engagement with said tapered distal tip of said non-luer tip catheter tip syringe to contact and open said valve and to prevent further downward movement of said tapered distal tip of said non-luer tip catheter tip syringe so as to prevent overstretching of said valve.

5. The closed system medical connector of claim 3, wherein said sealing engagement between said non-luer tip catheter tip syringe and said upper entrance port is a taper lock sealing engagement.

6. The closed system medical connector of claim 4, wherein said sealing engagement between said non-luer tip catheter tip syringe and said upper entrance port is a taper lock sealing engagement.

7. The closed system medical connector of claim 3, wherein said non-luer tip catheter tip syringe having downwardly inwardly rigid tapered outer wall portions forming the tapered distal tip terminating in a distal terminal end in turn defining a fluid opening, said tapered distal tip providing for either fluid infusion or fluid sampling through said closed system medical connector, said valve having a diaphragm with a slit opening including sides thereof and normally biased to a first sealed closed position thereby preventing fluid from exiting said lower fluid communication path and out said slit opening of said valve and said valve openable to a second open position by manual insertion of said tapered distal tip into engagement with said upper entrance port to enable said distal terminal end to progressively contact, downwardly bend and transverse through and maintain contact with said sides of said slit opening so as to thus hold open said valve.

8. The closed system medical connector of claim 4, wherein said non-luer tip catheter tip syringe having downwardly inwardly rigid tapered outer wall portions forming the tapered distal tip terminating in a distal terminal end in turn defining a fluid opening, said tapered distal tip providing for either fluid infusion or fluid sampling through said closed system medical connector, said valve having a diaphragm with a slit opening including sides thereof and normally biased to a first sealed closed position thereby preventing fluid from exiting said lower fluid communication path and out said slit opening of said valve and said valve openable to a second open position by manual insertion of said tapered distal tip into engagement with said upper entrance port to enable said distal terminal end to progressively contact, downwardly bend and transverse through and maintain contact with said sides of said slit opening so as to thus hold open said valve.

9. The closed system medical connector of claim 1, wherein said non-luer tip catheter tip syringe is a non-luer fluid delivery device having a catheter tip syringe configuration.

* * * * *